US012767645B2

(12) United States Patent
Luo et al.

(10) Patent No.: US 12,767,645 B2
(45) Date of Patent: Oct. 20, 2026

(54) PREPARATION METHOD FOR CANNFLAVIN COMPOUNDS

(71) Applicant: DEYI PHARMACEUTICAL LTD., Kunming (CN)

(72) Inventors: Junlu Luo, Kunming (CN); Hongtao Mou, Kunming (CN); Yesong Du, Kunming (CN); Xin Tan, Kunming (CN); Shubin Wang, Kunming (CN); Pingping Zhang, Kunming (CN); Lan Lan, Kunming (CN)

(73) Assignee: DEYI PHARMACEUTICAL LTD., Yunnan (CN)

( * ) Notice: Subject to any disclaimer, the term of this patent is extended or adjusted under 35 U.S.C. 154(b) by 573 days.

(21) Appl. No.: 18/252,300

(22) PCT Filed: Jan. 21, 2021

(86) PCT No.: PCT/CN2021/073145
§ 371 (c)(1),
(2) Date: May 9, 2023

(87) PCT Pub. No.: WO2022/099931
PCT Pub. Date: May 19, 2022

(65) Prior Publication Data

US 2023/0406834 A1 Dec. 21, 2023

(30) Foreign Application Priority Data

Nov. 12, 2020 (CN) ......................... 202011262162.4

(51) Int. Cl.
*C07D 311/30* (2006.01)

(52) U.S. Cl.
CPC ................................. *C07D 311/30* (2013.01)

(58) Field of Classification Search
CPC ................................................... C07D 311/30
See application file for complete search history.

(56) References Cited

U.S. PATENT DOCUMENTS 9,090,583 B2 7/2015 Ding

FOREIGN PATENT DOCUMENTS

| | | | |
|---|---|---|---|
| CN | 102018698 | A | 4/2011 |
| CN | 102558164 | A | 7/2012 |
| CN | 104031016 | A | 9/2014 |
| CN | 107686472 | A | 2/2018 |
| CN | 109369591 | A | 2/2019 |
| WO | 2017027136 | A2 | 2/2017 |
| WO | 2017091837 | A2 | 6/2017 |

OTHER PUBLICATIONS

Luis Espinoza et al., “Synthesis of Linear Geranylphenols and Their Effect on Mycelical Growth of Plant Pathogen Botrytis cinerea”, Molecules, vol. 19, No. 2, Jan. 27, 2014, pp. 1512-1526.
International Search Report for PCT/CN2021/073145 mailed Aug. 18, 2021, 7 pages w/English translation.
Written Opinion of the ISA for PCT/CN2021/073145 mailed Aug. 18, 2021, 4 pages.
Thévenin et al., “First total synthesis of original chalcone-flavone dimers as cissampeloflavone analogues”, Eur. J. Org. Chem. 10.1002/ejoc.201800338, published as vol. 2018, No. 42, Apr. 24, 2018 (Apr. 24, 2018), ISSN: 1099-0690, pp. 5843-5852.
Salem, et al., “Antiparasitic Activity of C-Geranyl Flavonoids from Mimulus 1-14 bigelovii”, Phytother. Res., vol. 25, No. 8, Feb. 1, 2011 (Feb. 1, 2011), ISSN: 1099-1573, pp. 1246-1249.
Notice of Allowance in U.S. Appl. No. 18/036,140 dated Mar. 12, 2026, 8 pages.
Non-Final Rejection in U.S. Appl. No. 18/036,140 dated Sep. 30, 2025, 23 pages.
Response to Non-Final Rejection in U.S. Appl. No. 18/036,140 filed Dec. 31, 2025, 12 pages.
Raikar et al., “Synthesis of Polyprenylated Benzoylphloroglucinols by Regioselective Prenylation of Phloroglucinol in an Aqueous Medium”, InterScience, European Journal of Organic Chemistry, 2008, 12 pages.
Errige et al., “Cannflavins—From plant to patient: A scoping review”, Elsevier, Aug. 25, 2020, 10 pages.

*Primary Examiner* — Golam M Shameem
(74) *Attorney, Agent, or Firm* — NIXON & VANDERHYE, PC

(57) ABSTRACT

Disclosed in the present invention is a preparation method for cannflavin compounds. The preparation method has advantages such as cheap and easily available raw materials, few reaction steps, short production period, and easy operation. The method comprises: first, condensing 4'-hydroxy-3'-methoxyacetophenone and diethyl carbonate (DEC) under an alkaline condition to obtain ethyl 4'-hydroxy-3'-methoxybenzoylacetate, next, reacting 1,3,5-trihydroxybenzene with geraniol to obtain (E)-2-(3,7-dimethyloct-2,6-dien-1-yl)benzene-1,3,5-triphenol; and finally, condensing ethyl 4'-hydroxy-3'-methoxybenzoylacetate and (E)-2-(3,7-dimethyloct-2,6-dien-1-yl)benzene-1,3,5-triphenol at high temperature to produce cannflavin A and/or cannflavin C, and then carrying out separation and purification to obtain pure cannflavin A and cannflavin C.

13 Claims, No Drawings

PREPARATION METHOD FOR CANNFLAVIN COMPOUNDS

CROSS-REFERENCE TO RELATED APPLICATIONS

This application is the U.S. national phase of International Application No. PCT/CN2021/073145 filed Jan. 21, 2021, which designated the U.S. and claims priority to CN 202011262162.4 filed Nov. 12, 2020, the entire contents of each of which are hereby incorporated by reference.

TECHNICAL FIELD

The present invention relates to the field of chemical synthesis, and particularly to a preparation method for a cannflavin compound, especially cannflavin A and/or cannflavin C.

BACKGROUND

Among over 200 biologically-active compounds of *Cannabis sativa*, cannabinoids and terpenes have been of greatest concern. However, there is another important compound in *Cannabis sativa*, that is cannflavin compounds which account for 10% of these known compounds, of which about 20 types are known to be present in *Cannabis sativa*, and these flavonoids have no psychoactive properties.

Studies proved that Cannflavin A has anti-inflammatory effects as early as 1985, and cannflavin C was discovered in 2008. In contrast to other analgesic agents, cannflavin A and cannflavin C do not induce a risk of drug dependence and addiction in patients.

The flavonoid backbone and geranyl group on the backbone of cannflavin A and cannflavin C can improve the lipophilicity of molecules, thereby enhancing cell uptake of the molecules and their accumulation in organisms, and promote the interaction between the molecules and cells, for example, the molecules participate in the transduction pathways of membrane-bound enzymes and receptor cell signals.

Moreau et al. reported in Flavonoid Derivative of *Cannabis* Demonstrates Therapeutic Potential in Preclinical Models of Metastatic Pancreatic Cancer. ([J]. Front. Oncol, 2019, 9: 660) that researchers extracted cannflavin A and cannflavin C as well as other flavonoids from local *Cannabis Sativa* L. strain in Jamaica with chromatography. The researchers performed in vitro and in vivo experiments on the extracts successively. In vivo experiment results showed therapeutic effects of delaying local and metastatic tumor progression in pancreatic cancer animal models when cannflavin compounds were provided continuously by using smart radiotherapy biomaterials. Compared with the control group, repeated tests also showed a significant increase in survival of pancreatic cancer animals. Research results showed that cannflavin A and cannflavin C have important therapeutic potential for the treatment of pancreatic cancer, including therapeutic potential for radiosensitization and tumor metastasis. These results provide the basis for further study and optimization of the therapeutic results in clinical trials. The content of flavonoids in the *Cannabis sativa* is much less than 1%, less than 0.14% on average, and the content of cannflavin A and cannflavin C in the *Cannabis sativa* is extremely low. Therefore, it is infeasible to rely solely on *Cannabis sativa* plant extraction to obtain these components. Currently, researchers are working on the preparation of these active factors based on biological systems, which will create a great deal of opportunities for cannflavins.

Barrett et al. reported in Cannflavin A and B, prenylated flavones from *Cannabis sativa* L. ([J]. Cellular & Molecular Life Sciences, 1986, 452-453) the separation of cannflavin A from an ethanol extract of *Cannabis sativa*, but the yield of cannflavin A was extremely low.

Rea et al. reported in Biosynthesis of cannflavins A and B from *Cannabis sativa* L. ([J]. Phytochemistry, 2019, 134, 162-171) the synthesis of cannflavin A from dimethylallyl diphosphate under the catalysis of aromatic prenyltransferase of *Sinorhizobium meliloti*. However, this biosynthesis method is costly and not easily scalable industrially.

Patent document WO2017091837 discloses a method as follows: synthesizing a main chain of cannflavin compounds by using a known chemical synthesis technology with 2,4,6-trihydroxyacetophenone as a starting reactant, then forming a tricyclic structure by conjugating and ring closing, and finally performing a series of enzymatic modifications to obtain cannflavin A, cannflavin C and other flavonoids.

The chemical synthesis methods disclosed have the defects of long synthesis steps, multi-step reactions requiring silica gel column chromatography for purification, and difficulty in amplification. Therefore, there is an urgent need for a novel method for synthesizing cannflavin A and cannflavin C, which is simple, rapid, and easily scale-up.

SUMMARY

The present invention provides a preparation method for a cannflavin compound. The preparation method has the advantages of cheap and easily available raw materials, few reaction steps, short production period, simple operation, etc.

The present invention aims to provide a preparation method for a cannflavin compound, which comprises the following steps:

condensing

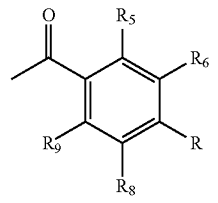

and diethyl carbonate under an alkaline condition to obtain

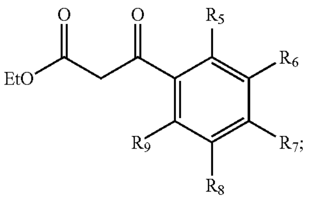

reacting

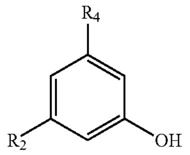

with an alcohol compound ($R_3$—OH) to obtain

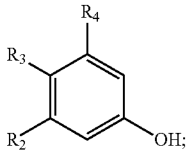

and reacting

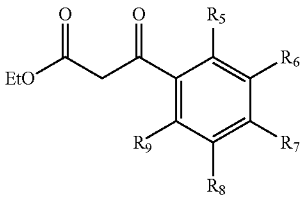

with

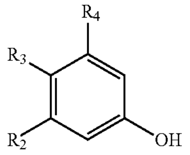

to obtain the cannflavin compound;

wherein the cannflavin compound has a structure of general formula I:

I

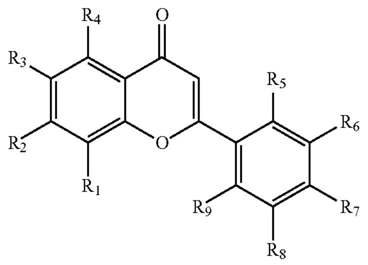

$R_5$, $R_6$, $R_7$, $R_8$, and $R_9$ are independently selected from the group consisting of: H, $C_{1-14}$ alkyl, $C_{3-14}$ alkenyl, hydroxy, $C_{1-5}$ alkoxy, carboxyl, amino, and halogen.

$R_2$ and $R_4$ are independently selected from the group consisting of: H, $C_{1-14}$ alkyl, $C_{3-14}$ alkenyl, hydroxy, $C_{1-5}$ alkoxy, carboxyl, and halogen.

$R_3$ and $R_1$ are independently selected from the group consisting of: H, $C_{1-14}$ alkyl, $C_{3-14}$ alkenyl, and $C_{1-5}$ alkoxy.

In one embodiment of the present invention, $R_3$ is geranyl.

In one embodiment of the present invention, $R_1$ is geranyl.

In one embodiment of the present invention, $R_2$ is hydroxy.

In one embodiment of the present invention, $R_4$ is hydroxy.

In one embodiment of the present invention, $R_7$ is hydroxy.

In one embodiment of the present invention, $R_6$ is methoxy.

In one embodiment of the present invention, $R_5$ is H.

In one embodiment of the present invention, $R_8$ is H.

In one embodiment of the present invention, $R_9$ is H.

Furthermore, the preparation method comprises the following steps:

condensing

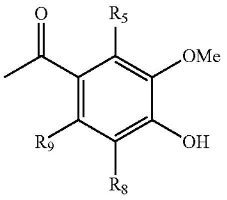

and diethyl carbonate under an alkaline condition to obtain

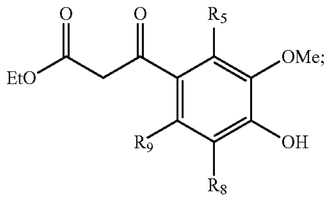

reacting

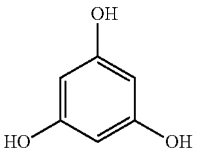

with an alcohol compound ($R_3$—OH) to obtain

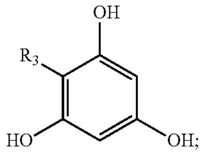

and reacting

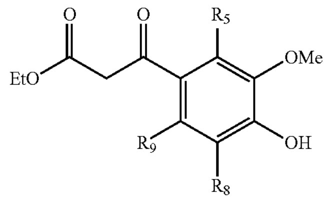

with

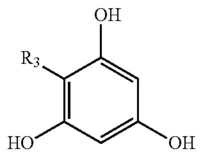

to obtain the cannflavin compound;

wherein the cannflavin compound has a structure of general formula II:

II

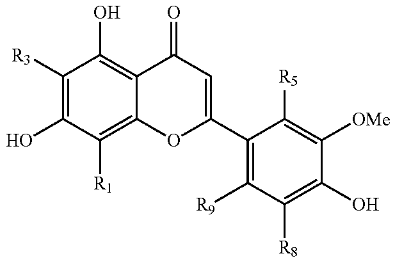

$R_5$, $R_8$, and $R_9$ are independently selected from the group consisting of: H, $C_{1-14}$ alkyl, $C_{3-14}$ alkenyl, hydroxy, $C_{1-5}$ alkoxy, carboxyl, amino, and halogen;

$R_3$ and $R_1$ are independently selected from the group consisting of: H, $C_{1-14}$ alkyl, $C_{3-14}$ alkenyl, and $C_{1-5}$ alkoxy.

Preferably, $R_3$ is geranyl; preferably, $R_5$ is H; preferably, $R_5$ is H; preferably, $R_9$ is H; and preferably, $R_1$ is geranyl.

The present invention also aims to provide a preparation method for cannflavin A and/or cannflavin C with 1,3,5-trihydroxybenzene and 4'-hydroxy-3'-methoxyacetophenone as starting materials, which comprises:

step (1): condensing 4'-hydroxy-3'-methoxyacetophenone and diethyl carbonate under an alkaline condition to obtain ethyl 4'-hydroxy-3'-methoxybenzoylacetate;

step (2): subjecting 1,3,5-trihydroxybenzene and geraniol to a C-alkylation reaction to obtain (E)-2-(3,7-dimethyloct-2,6-dien-1-yl)benzene-1,3,5-triphenol; and step (3): condensing ethyl 4'-hydroxy-3'-methoxybenzoylacetate and (E)-2-(3,7-dimethyloct-2,6-dien-1-yl)benzene-1,3,5-triphenol at high temperature to produce cannflavin A and/or cannflavin C.

The reaction equation of the step (2) is as follows:

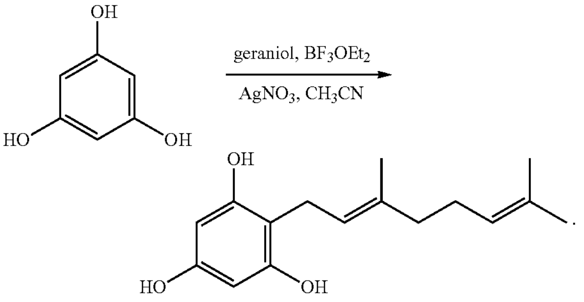

Preferably, in the step (2), the reaction is performed under an oxygen-free environment, and further, the inert gas is nitrogen or argon; the reaction system further comprises a solvent which is acetonitrile and/or diethyl ether; and in one embodiment of the present invention, the solvent is acetonitrile.

Preferably, in the step (2), the molar ratio of 1,3,5-trihydroxybenzene to geraniol is 1:3 to 3:1, and further, the molar ratio of 1,3,5-trihydroxybenzene to geraniol is 1:3, 1:2, 1:1, 2:1 or 3:1, and most preferably, 1:1.

Preferably, in the step (2), the reaction temperature is 0-25° C., and further, the reaction temperature is 0° C., 5° C., 10° C., 15° C., 20° C., or 25° C.

Preferably, in the step (2), the reaction time is 8-24 h, and further, the reaction time is 8 h, 12 h, 16 h, 20 h, or 24 h, and most preferably, 12 h.

Preferably, in the step (2), the reaction further requires the dropwise addition of a solution of boron trifluoride in diethyl ether.

In one embodiment of the present invention, the step (2) comprises the following specific steps: adding acetonitrile saturated with silver nitrate into a reaction vessel, then adding 1,3,5-trihydroxybenzene and geraniol, cooling under inert gas protection, adding dropwise a solution of boron trifluoride in diethyl ether, stirring, reacting, and then performing post-treatment on the resulting reaction liquid to obtain (E)-2-(3,7-dimethyloct-2,6-dien-1-yl)benzene-1,3,5-triphenol.

Preferably, the post-treatment comprises a quenching step.

More preferably, the quenching comprises the following specific step: adding an ice-water mixture to the reaction vessel.

More preferably, the quenching solvent is one or more selected from the group consisting of: an ice-water mixture, methyl tert-butyl ether, diethyl ether, ethyl acetate, and butyl acetate; and in one embodiment of the present invention, the quenching solvent is an ice-water mixture.

Preferably, the post-treatment further comprises an extraction step after the quenching step.

More preferably, the extraction solvent is one or more selected from the group consisting of: methyl tert-butyl ether, diethyl ether, ethyl acetate, and butyl acetate; and in one embodiment of the present invention, the extraction solvent is ethyl acetate.

More preferably, the extraction temperature is 5-40° C., and further preferably 15-25° C., and further, the extraction temperature is 15° C., 20° C., or 25° C.

In one embodiment of the present invention, the extraction step comprises the following specific steps: adding an extraction solvent into the reaction liquid, and layering; adding an extraction solvent to the aqueous layer for extraction, and layering; and combining the organic layers, washing, layering, and then combining the organic layers.

Preferably, the post-treatment further comprises a distillation step after the extraction step; and more preferably, the distillation step comprises steps of atmospheric distillation and vacuum distillation.

Preferably, the vacuum distillation temperature is 20-50° C., and the vacuum degree is −0.1 MPa to −0.05 MPa.

Preferably, the post-treatment further comprises a column chromatography step in sequence after the distillation step; and more preferably, the column chromatography step comprises normal-phase column chromatography and reverse-phase column chromatography.

More preferably, the column chromatography is normal-phase column chromatography, and the eluent in the column chromatography is selected from the group consisting of: petroleum ether, n-hexane, ethyl acetate, toluene, triethylamine, dichloromethane, water, and methanol; and in one embodiment of the present invention, the eluent is petroleum ether (PE) and ethyl acetate (EA), and the ratio of the eluent is PE:EA=8:1→4:1→2:1.

In a preferred embodiment of the present invention, the post-treatment comprises: quenching, extraction, distillation, and column chromatography in sequence, wherein the specific operation and conditions of each step are as described above in the present invention.

In one embodiment of the present invention, the preparation method for (E)-2-(3,7-dimethyloct-2,6-dien-1-yl)benzene-1,3,5-triphenol comprises the following steps:

(2-1) reaction step: adding acetonitrile saturated with silver nitrate into a reaction vessel, then adding 1,3,5-trihydroxybenzene and geraniol, cooling under inert gas protection, adding dropwise a solution of boron trifluoride in diethyl ether, stirring, heating to room temperature, and reacting for 8-24 h;

(2-2) control step: adding an ice-water mixture into the mixture of (2-1), and layering; adding ethyl acetate to the aqueous layer for extraction, and layering; combining the organic layers, washing with saturated brine, and layering; and combining the organic layers, drying over anhydrous sodium sulfate, filtering under vacuum, and concentrating the filtrate; and (2-3): separating the concentrate of the step (2-2) by column chromatography (silica gel 200-300 mesh, PE:EA=8:1-4:1→2:1) to obtain (E)-2-(3,7-dimethyloct-2,6-dien-1-yl)benzene-1,3,5-triphenol.

The reaction equation of the step (3) is as follows:

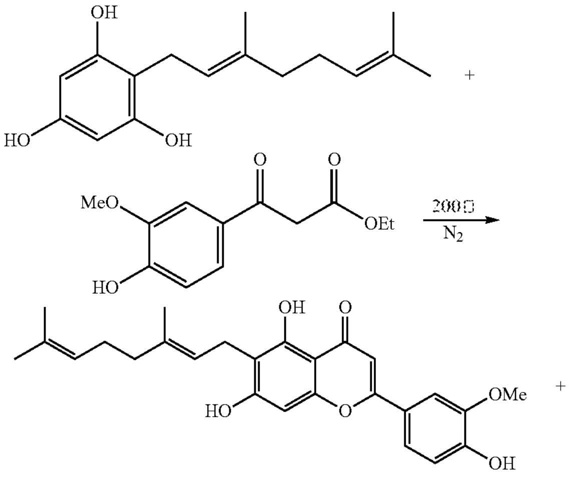

cannflavin A

-continued

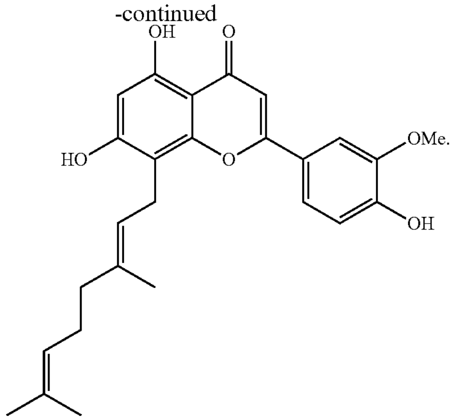

cannflavin C

Preferably, in the step (3), the reaction environment is an oxygen-free environment; more preferably, the reaction environment is an inert gas protected reaction environment; and in one embodiment of the present invention, the reaction environment is a nitrogen protected reaction environment.

Preferably, in the step (3), the reaction temperature is 150-230° C.; further, the reaction temperature is 160° C., 180° C., 200° C., or 220° C.; and in one embodiment of the present invention, the reaction temperature is 200° C.

Preferably, in the step (3), the reaction time is 2-8 h; further, the reaction time is 3 h, 5 h, or 7 h; and in one embodiment of the present invention, the reaction time is 3 h.

Preferably, in the step (3), the molar ratio of ethyl 4'-hydroxy-3'-methoxybenzoylacetate to (E)-2-(3,7-dimethyloct-2,6-dien-1-yl)benzene-1,3,5-triphenol is 1:3 to 3:1, and further, the molar ratio of ethyl 4'-hydroxy-3'-methoxybenzoylacetate to (E)-2-(3,7-dimethyloct-2,6-dien-1-yl)benzene-1,3,5-triphenol is 1:3, 1:2, 1:1, 1.5:1, 2:1, or 3:1, and most preferably, 1.5:1.

In one embodiment of the present invention, the step (3) comprises the following specific steps: under inert gas protection, adding ethyl 4'-hydroxy-3'-methoxybenzoylacetate and (E)-2-(3,7-dimethyloct-2,6-dien-1-yl)benzene-1,3,5-triphenol into a reaction vessel, stirring, heating, reacting, and then performing post-treatment on the resulting reaction liquid to obtain cannflavin A and/or cannflavin C.

Preferably, the post-treatment further comprises a column chromatography step; more preferably, the column chromatography step comprises normal-phase column chromatography and reverse-phase column chromatography.

More preferably, the column chromatography step comprises the following steps: subjecting the mixture to normal-phase silica gel column chromatography multiple times, followed by reverse-phase silica gel column chromatography multiple times.

More preferably, the eluent in the column chromatography is selected from the group consisting of: petroleum ether, n-hexane, ethyl acetate, toluene, triethylamine, dichloromethane, water, and methanol; in one embodiment of the present invention, the eluent in the normal-phase silica gel column chromatography is petroleum ether (PE) and ethyl acetate (EA), and the ratio of the eluent is PE:EA=10:1→2:1, and the eluent in the reverse-phase silica gel column chromatography is water and methanol, and the ratio of the eluent is water:methanol=50:50→40:90.

Preferably, the post-treatment further comprises a recrystallization step after the column chromatography step; and more preferably, the recrystallization step comprises steps of dissolution and cooling to precipitate.

More preferably, the solvent for dissolution is one or a mixture of more selected from the group consisting of: toluene, methanol, acetone, water, etc.; and in one embodiment of the present invention, the solvent is methanol.

More preferably, the dissolution temperature is 40-100° C., and further preferably, 60-100° C.; and in one embodiment of the present invention, the dissolution temperature is 65° C.

More preferably, the step of cooling to precipitate comprises cooling to 1-30° C.; and in one embodiment of the present invention, the step of cooling to precipitate comprises cooling to 18-22° C.

In one embodiment of the present invention, the recrystallization step comprises the following steps: adding a solvent, heating to 40-100° C., dissolving the solid completely, cooling to 1-30° C., precipitating, and filtering the precipitate.

Preferably, the post-treatment further comprises a drying step after the recrystallization step.

More preferably, the drying step is vacuum drying; and more preferably, the vacuum degree is −0.08 MPa to −0.01 MPa.

More preferably, the drying temperature is 45-65° C.

In a preferred embodiment of the present invention, the post-treatment comprises: column chromatography, recrystallization, and drying in sequence, wherein the specific operation and conditions of each step are as described above in the present invention.

In one specific embodiment of the present invention, the preparation method for cannflavin A and/or cannflavin C comprises the following steps:

- (3-1) reaction step: under nitrogen protection, adding ethyl 4'-hydroxy-3'-methoxybenzoylacetate and (E)-2-(3,7-dimethyloct-2,6-dien-1-yl)benzene-1,3,5-triphenol into a reaction vessel, stirring, heating to 150-230° C., and reacting for 2-8 h;
- (3-2): cooling to room temperature, subjecting the mixture to normal-phase silica gel column chromatography multiple times, followed by reverse-phase silica gel column chromatography multiple times, and evaporating the product to dryness;
- (3-3): adding methanol into the evaporated product obtained in the step (3-2), heating to dissolving the solid completely, cooling to 18-22° C., precipitating the solid, filtering, and rinsing the filter cake; and
- (3-4): drying the filter cake obtained in the step (3-3) under vacuum at 50-55° C.

Preferably, ethyl 4'-hydroxy-3'-methoxybenzoylacetate is prepared by the following step: condensing 4'-hydroxy-3'-methoxyacetophenone and diethyl carbonate under an alkaline condition to obtain ethyl 4'-hydroxy-3'-methoxybenzoylacetate.

The reaction equation of the step (1) is as follows:

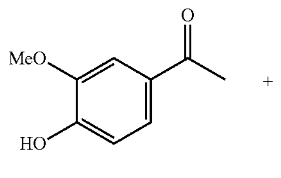

-continued

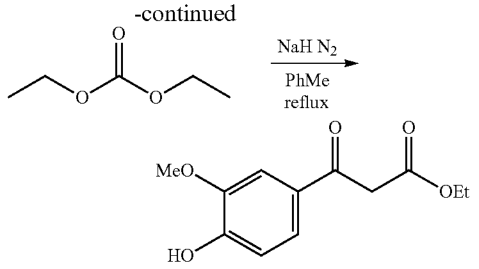

Preferably, in the step (1), the reaction is performed under an alkaline condition, and more preferably, the alkaline condition is that an alkali, such as an inorganic alkali, is included in the reaction system, and the inorganic alkali is one or a mixture of more selected from the group consisting of: pure inorganic alkali of sodium hydride and paraffin oil-coated sodium hydride; and in one embodiment of the present invention, the inorganic alkali is paraffin oil-coated sodium hydride.

More preferably, the mass molar ratio of the alkali to 4'-hydroxy-3'-methoxyacetophenone is g/mol, and further preferably, 100-150 g/mol; and further, the mass molar ratio of the alkali to 4'-hydroxy-3'-methoxyacetophenone is 100 g/mol, 110 g/mol, 120 g/mol, 130 g/mol, 140 g/mol, or 150 g/mol.

Preferably, in the step (1), the reaction system further comprises a solvent selected from the group consisting of: toluene and/or benzene: and in one embodiment of the present invention, the solvent is toluene.

Preferably, in the step (1), the molar ratio of 4'-hydroxy-3'-methoxyacetophenone to diethyl carbonate is 1:3 to 3:1, and further, the molar ratio of 4'-hydroxy-3'-methoxyacetophenone to diethyl carbonate is 1:3, 1:2, 1:1, 2:1, or 3:1, and most preferably, 1:2.

Preferably, in the step (1), the reaction environment is an oxygen-free environment; more preferably, the reaction environment is an inert gas protected reaction environment; and in one embodiment of the present invention, the reaction environment is a nitrogen protected reaction environment.

Preferably, in the step (1), the reaction temperature is 80-130° C., and further, the reaction temperature is 80° C., 90° C., 100° C., 110° C., 120° C., or 130° C.

Preferably, in the step (1), the reaction time is 2-12 h, and further, the reaction time is 4 h, 6 h, 8 h, 10 h, or 12 h, and most preferably, 4 h.

Preferably, in the step (1), 4'-hydroxy-3'-methoxyacetophenone is added dropwise to diethyl carbonate.

In one embodiment of the present invention, the preparation method comprises the following specific steps: under nitrogen protection, adding 60% NaH and toluene into a reaction vessel, stirring, adding diethyl carbonate, heating, adding dropwise a mixture of 4'-hydroxy-3'-methoxyacetophenone and toluene, stirring, reacting, and then performing post-treatment on the resulting reaction liquid to obtain ethyl 4'-hydroxy-3'-methoxybenzoylacetate.

Preferably, the post-treatment comprises a quenching step.

More preferably, the quenching comprises the following specific step: adding an acid to the reaction vessel to adjust pH of the mixture to 4.0-7.0.

More preferably, the acid is an inorganic acid which is one or a mixture of more selected from the group consisting of: pure inorganic acid of acetic acid and an aqueous solution thereof; and in one embodiment of the present invention, the acid is acetic acid.

Preferably, the post-treatment further comprises an extraction step after the quenching step.

More preferably, the extraction solvent is one or more selected from the group consisting of: methyl tert-butyl ether, diethyl ether, ethyl acetate, and butyl acetate; and in one embodiment of the present invention, the extraction solvent is ethyl acetate.

More preferably, an extraction temperature is 5-40° C., and further preferably, 15-25° C.

In one embodiment of the present invention, the extraction step comprises the following specific steps: adding an extraction solvent into the reaction liquid, and layering; adding an extraction solvent to the aqueous layer for extraction, and layering; and combining the organic layers, washing, layering, and then combining the organic layers.

Preferably, the post-treatment further comprises a distillation step after the extraction step; and more preferably, the distillation step comprises steps of atmospheric distillation and vacuum distillation.

Preferably, the vacuum distillation temperature is 20-50° C., and the vacuum degree is −0.1 MPa to −0.05 MPa.

Preferably, the post-treatment further comprises washing in sequence after the distillation step; more preferably, the washing solvent is selected from the group consisting of: n-hexane and/or diethyl ether; and in one embodiment of the present invention, the washing solvent is n-hexane.

In a preferred embodiment of the present invention, the post-treatment comprises: quenching, extraction, distillation and washing in sequence, wherein the specific operation and conditions of each step are as described above in the present invention.

In one embodiment of the present invention, the preparation method for ethyl 4'-hydroxy-3'-methoxybenzoylacetate comprises the following steps:

(1-1) reaction step: under nitrogen protection, adding 60% NaH and toluene into a reaction vessel, stirring, adding diethyl carbonate, heating to 80-130° C., adding dropwise a mixture of 4'-hydroxy-3'-methoxyacetophenone and toluene, stirring, and reacting for 2-12 h;

(1-2) control step: adding acetic acid to the mixture of (1-1) to adjust pH to 4.0-7.0, adding ethyl acetate, and layering; adding ethyl acetate to the aqueous layer for extraction, layering, combining the organic layers, washing with saturated ammonium chloride aqueous solution and saturated brine, layering, combining the organic layers, drying over anhydrous sodium sulfate, filtering under vacuum, and concentrating the filtrate; and (1-3) adding the concentrate obtained in the step (1-2) into n-hexane, stirring for 2-12 h, and filtering to obtain ethyl 4'-hydroxy-3'-methoxybenzoylacetate.

The present invention further provides a preparation method for cannflavin compounds, which comprises the preparation step of (E)-2-(3,7-dimethyloct-2,6-dien-1-yl) benzene-1,3,5-triphenol described above.

The present invention further provides use of ethyl 4'-hydroxy-3'-methoxybenzoylacetate in preparing a compound, wherein the compound is cannflavin A and/or cannflavin C.

The present invention has the advantages of cheap and easily available raw materials, simple synthetic route, simple operation, short production period, and relatively low synthetic cost, and thus has certain economic value.

DETAILED DESCRIPTION

It should be noted that the detailed description as follows is exemplary and is intended to provide further explanation of the present application. Unless otherwise stated, all technical and scientific terms used herein have the same meaning as that commonly understood by those of ordinary skill in the art to which the present application belongs.

Example 1: Synthesis of Ethyl 4'-hydroxy-3'-methoxybenzoylacetate

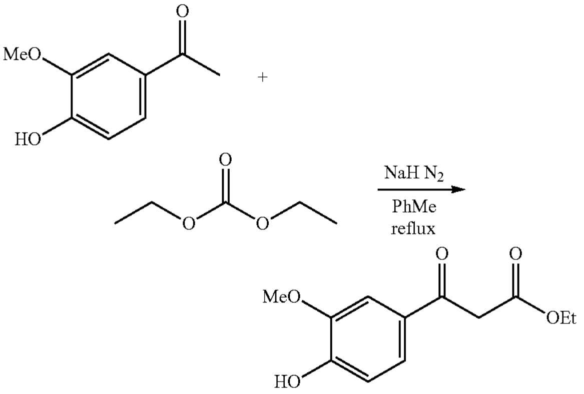

To a reaction flask, 60% NaH (6.00 g, 150 mmol) was added, under nitrogen protection, toluene (60 mL) and DEC (11.82 g, 100 mmol) were added, and the resulting mixture was stirred, and heated to reflux. A solution of 4'-hydroxy-3'-methoxyacetophenone (12.82 g, 50 mmol) in toluene (60 mL) was added dropwise. After the addition was completed, the resulting mixture was refluxed for 4 h, then cooled to room temperature, adjusted to pH neutral with acetic acid, and added with a saturated ammonium chloride aqueous solution (150 mL). The aqueous phase was extracted with ethyl acetate (100 mL×3). The organic phases were combined, and washed successively with a saturated ammonium chloride aqueous solution (100 mL×2) and saturated brine (100 mL×2). The resulting organic phase was dried over anhydrous sodium sulfate, and filtered under vacuum. The filtrate was concentrated to dryness, added with n-hexane (50 mL), stirred overnight, and filtered to obtain ethyl 4'-hydroxy-3'-methoxybenzoylacetate (15.43 g, 93.9%) as an orange-yellow solid. MS (ESI): 238.9 $[M+H]^+$.

Example 2: Synthesis of (E)-2-(3,7-dimethyloct-2,6-dien-1-yl)benzene-1,3,5-triphenol

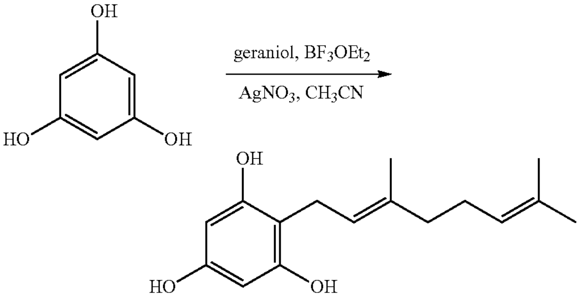

To a reaction flask, 50 mL of acetonitrile saturated with silver nitrate was added and stirred. 1,3,5-trihydroxybenzene (3.33 g, 26.41 mmol) and geraniol (4.08 g, 26.45 mmol)

were added. Under nitrogen protection, the resulting mixture was cooled in an ice-water bath, followed by dropwise addition of a solution of boron trifluoride in diethyl ether (1.23 g, 8.85 mmol). After the addition was completed, the resulting mixture was stirred at room temperature overnight. The reaction liquid was poured into 50 mL of ice-water mixture, and extracted with ethyl acetate (30 mL×3). The organic phases were combined, washed successively with 5% aqueous sodium bicarbonate solution and water (20 mL×3), dried over anhydrous sodium sulfate, and filtered under vacuum. The filtrate was concentrated to dryness, and the resulting oil was subjected to column chromatography (silica gel 200-300 mesh, petroleum ether:ethyl acetate=8:1→4:1→2:1) to obtain (E)-2-(3,7-dimethyloct-2,6-dien-1-yl)benzene-1,3,5-triphenol as an oil (0.6 g). MS (ESI): 263.2 $[M+H]^+$.

Example 3: Synthesis of Cannflavin A and/or Cannflavin C

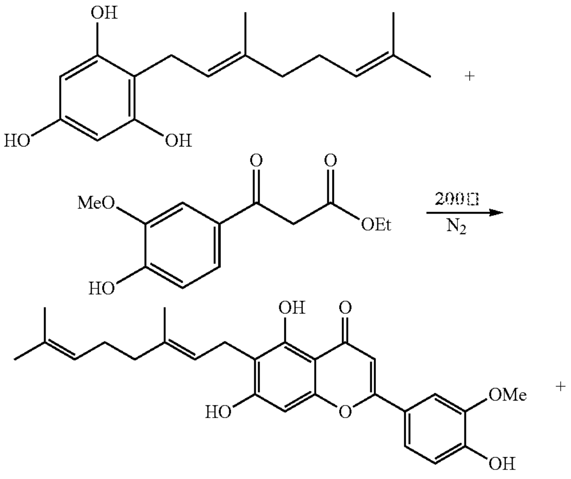

cannflavin A

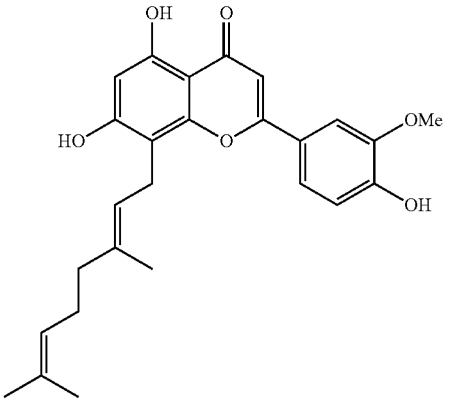

cannflavin C

To a reaction flask, (E)-2-(3,7-dimethyloct-2,6-dien-1-yl) benzene-1,3,5-triphenol (3.8 g, mmol) and ethyl 4'-hydroxy-3'-methoxybenzoylacetate (2.8 g, 10.67 mmol) were added and stirred. Under nitrogen protection, the resulting mixture was heated to 200° C., and maintained at this temperature for 3 h. The reaction mixture was cooled to room temperature, and the resulting product was purified by normal-phase silica gel column chromatography (silica gel 200-300 mesh, petroleum ether:ethyl acetate=10:1→2:1) multiple times and then purified by reverse-phase silica gel column chromatography (reverse-phase silica gel 200-300 mesh, water:methanol=50:50→40:90) multiple times to obtain cannflavin A (0.3227 g) and cannflavin C (0.2048 g) as yellow solids.

Cannflavin A: MS (ESI): MS (ESI): 437.0[M+H]+, $^1$H-NMR (Acetone-$d_6$, 400 MHz), δ: 1.56 (3H, s), 1.61 (3H, s), 1.81 (3H, s), 1.96 (2H, m), 2.04 (2H, m), 3.37 (2H, d), 4.00 (3H, s), 5.06 (1H, t), 5.29 (1H, t), 6.62 (1H, s), 6.70 (1H, s), 7.00 (1H, d), 7.58 (1H, dd), 7.60 (1H, d), 8.49 (1H, s), 9.56 (1H, s), 13.05. (1H, s).

Cannflavin C: MS (ESI): 437.0[M+H]+, $^1$H-NMR (Acetone-$d_6$, 400 MHz), δ: 1.50 (3H, s), 1.52 (3H, s), 1.84 (3H, s), 1.97 (2H, m), 2.03 (2H, m), 359(2H, d), 4.01 (3H, s), 5.04 (1H, t), (1H, t), 6.35 (1H, s), 6.72 (1H, s), 7.03 (1H, d), 7.63 (1H, dd), 7.64 (1H, d), 8.54 (1H, s), 9.63 (1H, s), 12.98. (1H, s).

The above descriptions are only preferred examples of the present application and are not intended to limit the present invention, and various modifications and changes may be made by those skilled in the art. Any modifications, equivalent replacements, improvements, and the like that are made within the spirit and principle of the present application shall all fall within the protection scope of the present application.

The invention claimed is:

1. A preparation method for a cannflavin compound, comprising the following steps:

step (1): condensing 4'-hydroxy-3'-methoxyacetophenone and diethyl carbonate under an alkaline condition to obtain ethyl 4'-hydroxy-3'-methoxybenzoylacetate;

step (2): subjecting 1,3,5-trihydroxybenzene and geraniol to a C-alkylation reaction to obtain (E)-2-(3,7-dimethyloct-2,6-dien-1-yl)benzene-1,3,5-triphenol; wherein the reaction is performed under an oxygen-free environment; and the reaction system further comprises a solvent selected from the group consisting of: acetonitrile and/or diethyl ether; and the reaction further comprises dropwise addition of a solution of boron trifluoride in diethyl ether; and step (3): condensing ethyl 4'-hydroxy-3'-methoxybenzoylacetate and (E)-2-(3,7-dimethyloct-2,6-dien-1-yl)benzene-1,3,5-triphenol at a reaction temperature of 180-230° C. to produce cannflavin A and/or cannflavin C;

wherein cannflavin A is represented by a formula:

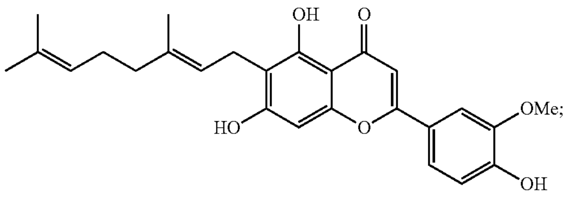 [SMILES: COc1cc(-c2cc(=O)c3c(O)c(C/C=C(\C)CCC=C(C)C)c(O)cc3o2)ccc1O]

and cannflavin C is represented by a formula:

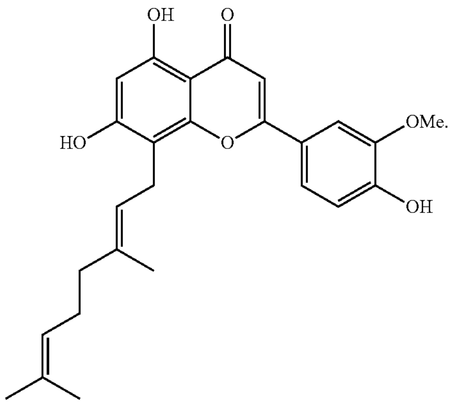 [SMILES: COc1cc(-c2cc(=O)c3c(O)cc(O)c(C/C=C(\C)CCC=C(C)C)c3o2)ccc1O]

2. The preparation method according to claim 1, wherein the step (1) comprises a step of reacting 4'-hydroxy-3'-methoxyacetophenone with diethyl carbonate; the reaction is performed under an oxygen-free environment; the reaction is performed under an alkaline condition; the reaction system further comprises a solvent selected from the group consisting of: toluene and/or benzene.

3. The preparation method according to claim 2, wherein the oxygen-free environment in the step (1) is an inert gas protected reaction environment;

the alkali is an inorganic alkali;

a mass molar ratio of the inorganic alkali to 4'-hydroxy-3'-methoxyacetophenone is 50-1000 g/mol;

a molar ratio of 4'-hydroxy-3'-methoxyacetophenone to diethyl carbonate is 1:3 to 3:1;

the reaction temperature is 80-130° C.;

the reaction time is 2-12 h; and

4'-hydroxy-3'-methoxyacetophenone is added dropwise to diethyl carbonate.

4. The preparation method according to claim 1, wherein the step (1) comprises the following steps: under inert gas protection, adding NaH and toluene into a reaction vessel, stirring, adding diethyl carbonate, heating, adding dropwise a mixture of 4'-hydroxy-3'-methoxyacetophenone and toluene, stirring, reacting, and then performing post-treatment on the resulting reaction liquid to obtain ethyl 4'-hydroxy-3'-methoxybenzoylacetate.

5. The preparation method according to claim 1, wherein the solvent of step (2) is acetonitrile.

6. The preparation method according to claim 1, wherein the oxygen-free environment in the step (2) is an inert gas protected reaction environment, the inert gas is nitrogen;

a molar ratio of 1,3,5-trihydroxybenzene to geraniol is 1:3 to 3:1;

the reaction temperature is 0-25° C.; and the reaction time is 8-24 h.

7. The preparation method according to claim 1, wherein the step (2) comprises the following steps: adding acetonitrile saturated with silver nitrate into a reaction vessel, then adding 1,3,5-trihydroxybenzene and geraniol, cooling under inert gas protection, adding dropwise a solution of boron trifluoride in diethyl ether, stirring, reacting, and then performing post-treatment on the resulting reaction liquid to obtain (E)-2-(3,7-dimethyloct-2,6-dien-1-yl)benzene-1,3,5-triphenol.

8. The preparation method according to claim 1, wherein the step (3) comprises a step of reacting ethyl 4'-hydroxy-3'-methoxybenzoylacetate with (E)-2-(3,7-dimethyloct-2,6-dien-1-yl)benzene-1,3,5-triphenol, wherein the reaction is performed under an oxygen-free environment.

9. The preparation method according to claim 8, wherein the oxygen-free environment in the step (3) is an inert gas protected reaction environment;

the reaction time is 2-8 h; and a molar ratio of ethyl 4'-hydroxy-3'-methoxybenzoylacetate to (E)-2-(3,7-dimethyloct-2,6-dien-1-yl)benzene-1,3,5-triphenol is 1:3 to 3:1.

10. The preparation method according to claim 1, wherein the step (3) comprises the following steps: under inert gas protection, adding ethyl 4'-hydroxy-3'-methoxybenzoylacetate and (E)-2-(3,7-dimethyloct-2,6-dien-1-yl)benzene-1,3,5-triphenol into a reaction vessel, stirring, heating, reacting, and then performing post-treatment on the resulting reaction liquid to obtain cannflavin A and/or cannflavin C.

11. The preparation method according to claim 1, comprising the following steps:

condensing 4'-hydroxy-3'-methoxyacetophenone and diethyl carbonate under an alkaline condition to obtain ethyl 4'-hydroxy-3'-methoxybenzoylacetate;

adding acetonitrile saturated with silver nitrate into a reaction vessel, then adding 1,3,5-trihydroxybenzene and geraniol, cooling under inert gas protection, adding dropwise a solution of boron trifluoride in diethyl ether, stirring, reacting, and then performing post-treatment on the resulting reaction liquid to obtain (E)-2-(3,7-dimethyloct-2,6-dien-1-yl)benzene-1,3,5-triphenol;

under inert gas protection, adding ethyl 4'-hydroxy-3'-methoxybenzoylacetate and (E)-2-(3,7-dimethyloct-2,6-dien-1-yl)benzene-1,3,5-triphenol into a reaction vessel, stirring, heating, reacting, and then performing post-treatment on the resulting reaction liquid to obtain cannflavin A and/or cannflavin C.

12. The preparation method according to claim 4, wherein the post-treatment comprises a quenching step; and the quenching step comprises: adding an acid to the reaction vessel to adjust pH of the mixture to 4.0-7.0.

13. The preparation method according to claim 7, wherein the post-treatment comprises a quenching step; and the quenching step comprises: adding a quenching solvent to the reaction vessel.

* * * * *